(12) United States Patent
Alley

(10) Patent No.: US 6,470,213 B1
(45) Date of Patent: Oct. 22, 2002

(54) IMPLANTABLE MEDICAL DEVICE

(76) Inventor: Kenneth A. Alley, RD 4, Box 4820, Berwick, PA (US) 18603

( * ) Notice: Subject to any disclaimer, the term of this patent is extended or adjusted under 35 U.S.C. 154(b) by 0 days.

(21) Appl. No.: 09/282,096

(22) Filed: Mar. 30, 1999

(51) Int. Cl.$^7$ ................................................ A61N 1/00

(52) U.S. Cl. .......................................... 607/41; 607/60

(58) Field of Search .................... 128/903, DIG. 25; 600/29, 30, 31, 135, 561, 585, 587; 601/4, 151, 152, 153; 604/66, 67; 607/40, 41; 606/191, 192, 46, 47

(56) References Cited

U.S. PATENT DOCUMENTS 3,642,004 A * 2/1972 Osthagen et al. .... 128/DIG. 25
5,704,353 A * 1/1998 Kalb et al. .................... 600/30

* cited by examiner

Primary Examiner—Jeffrey R. Jastrzab
(74) Attorney, Agent, or Firm—Mark A Garzia, P.C.

(57) ABSTRACT

A method is taught for communicating information between a bladder disposed within an individual and the exterior of the individual. The method includes providing an implantable medical device having an operating component for performing operations within the bladder, a communication device for providing a communication regarding the operation between the implantable medical device and the exterior of the individual, and an energy source for applying energy to the implantable medical device. The method also includes inserting at least a portion of the implantable medical device into the bladder of the individual by way of the urinary tract of the individual. The step of performing the operation and communicating the information regarding the operation from within the bladder to the exterior of the individual by the implantable medical device is also set forth. The operating component can be a sensor for sensing a parameter of the bladder such as, for example, a pressure sensor for sensing the pressure within the bladder or a temperature sensor for sensing the temperature within the bladder. Furthermore, the operating component can be a valve such as a fluid valve adapted to prevent a flow of fluid from the bladder of the individual. The fluid valve can be operated in accordance with the sensor. The pressure level determination is communicated to the exterior of the body of the individual. A control signal is transmitted from the exterior of the body of the individual to the implantable medical device within the body of the individual in accordance with the communicated pressure level determination. The fluid valve is operated in accordance with the control signal from the exterior of the body.

6 Claims, 1 Drawing Sheet

IMPLANTABLE MEDICAL DEVICE

BACKGROUND OF THE INVENTION

I. Field of the Invention

This invention relates to the field of medical devices and, in particular, to the field of implantable medical devices.

II. Prior Art

It is well know in the prior art to provide assistance to individuals having urinary incontinence. Urinary incontinence can be caused when malfunction of the sphincter muscles of the bladder or when malfunction of involved nerves prevent an individual from adequately controlling liquid wastes. This can result in discomfort and frequent trips to a bathroom. It can even require the use of diapers.

One very well known type of urinary medical device for assisting in the treatment of urinary incontinence is the Foley catheter. The Foley catheter is routinely used for incontinence and for other purposes when patients are admitted to hospitals. The Foley catheter includes a long tube connected to a waste reservoir. The tube is inserted into the urinary tract of a patient and serves as a conduit for the passage of liquid waste from the bladder of the individual to the waste reservoir that holds the liquid waste for later disposal.

However, one problem with the Foley catheter is that the inserted tube provides a pathway for bacteria as it passes through the urinary tract. There is an extremely high infection rate for individuals who use the Foley catheter for any significant period of time. The infections caused by Foley catheters in this manner can require treatment with antibiotics and can require the catheters to be replaced on a frequent basis.

Additionally, Foley catheters can prevent the user from engaging in many normal and beneficial activities. The user is restricted from these activities because the tube and the waste reservoir can be bulky and can hamper movement. Furthermore, mishandling of the waste reservoir can result in back flow of liquid waste from the waste reserve into the individual using the catheter.

It is also known in the prior art to provide implantable medical devices that communicate with the exterior of a body using RF communication techniques. Known implantable devices have power sources including rechargeable power sources as well as transmitters for transmitting the data to external receivers. Implantable devices of this nature include, for example, the following.

A device taught in U.S. Pat. No. 3,209,081, issued to Ducote discloses an implantable medical device with power supplied to amplifier transistors of an implanted radio device. Additionally, Stasz et al., U.S. Pat. No. 3,920,025, discloses a system having a low frequency transmitter, a low frequency receiver, and a power transmitter controlled by the low frequency receiver.

Schulman, U.S. Pat. No. 3,942,535, discloses an implantable system with a telemetry controlled power source. An externally located recharging device charges a charging circuit located beneath the skin of the patient that recharges a battery powering an electronic generator in the device taught by Schulman. A telemetry circuit connected to the charging circuit provides a magnetic output signal controlling externally located means associated with the power source. The external means in response to this signal provides a visual or audio indication of proper operation and positioning of external devices with respect to the implanted device.

Grevious, U.S. Pat. No. 5,168,871, discloses an external device for receiving data from an implanted medical device that measures various parameters within the body of a patient. Miller, U.S. Pat. No. 5,350,413, discloses an implantable device that transfers data from the interior of a patient to the exterior through a boundary layer using infrared signals. In order to perform this function a plurality of transmitters are arranged in a circular pattern on one side of the boundary layer and a receiver is positioned within the circular pattern along the opposite side of the boundary layer.

SUMMARY OF THE INVENTION

A method is taught for communicating information between a bladder within an individual and the exterior of the individual. The method includes providing an implantable medical device having an operating component for performing operations within the bladder, a communication device for providing a communication regarding the operation between the implantable medical device and the exterior of the individual, and an energy source for applying energy to the implantable medical device. The method also includes inserting at least a portion of the implantable medical device into the bladder of the individual by way of the urinary tract of the individual. The step of performing the operation and communicating the information regarding the operation from within the bladder to the exterior of the individual by the implantable medical device is also set forth. The operating component can be a sensor for sensing a parameter of the bladder such as, for example, a pressure sensor for sensing the pressure within the bladder or a temperature sensor for sensing the temperature within the bladder. Furthermore, the operating component can be a valve such as a fluid valve adapted to prevent a flow of fluid from the bladder of the individual. The fluid valve can be operated in accordance with the sensor. For example, a determination can be made that the pressure within the bladder has reached a predetermined level and that fluid flow from the bladder of the individual can be permitted in response to the pressure level determination. The pressure level determination is communicated to the exterior of the body of the individual. A control signal is transmitted from the exterior of the body of the individual to the implantable medical device within the body of the individual in accordance with the communicated pressure level determination. The fluid valve is operated in accordance with the control signal from the exterior of the body. In a preferred embodiment the implantable medical device includes an implantable receiver for receiving data from the exterior of the body of the individual and a plurality of operating components for receiving by the implantable receiver an instruction provided in accordance with at least one operating component and operating at least one operating component in accordance with the received instruction.

BRIEF DESCRIPTION OF THE DRAWINGS

The features, objects, and advantages of the present invention will become more apparent from the detailed description set forth below when taken in conjunction with the drawings in which like reference characters identify corresponding elements throughout and wherein.

DETAILED DESCRIPTION OF THE INVENTION

Figure 1:
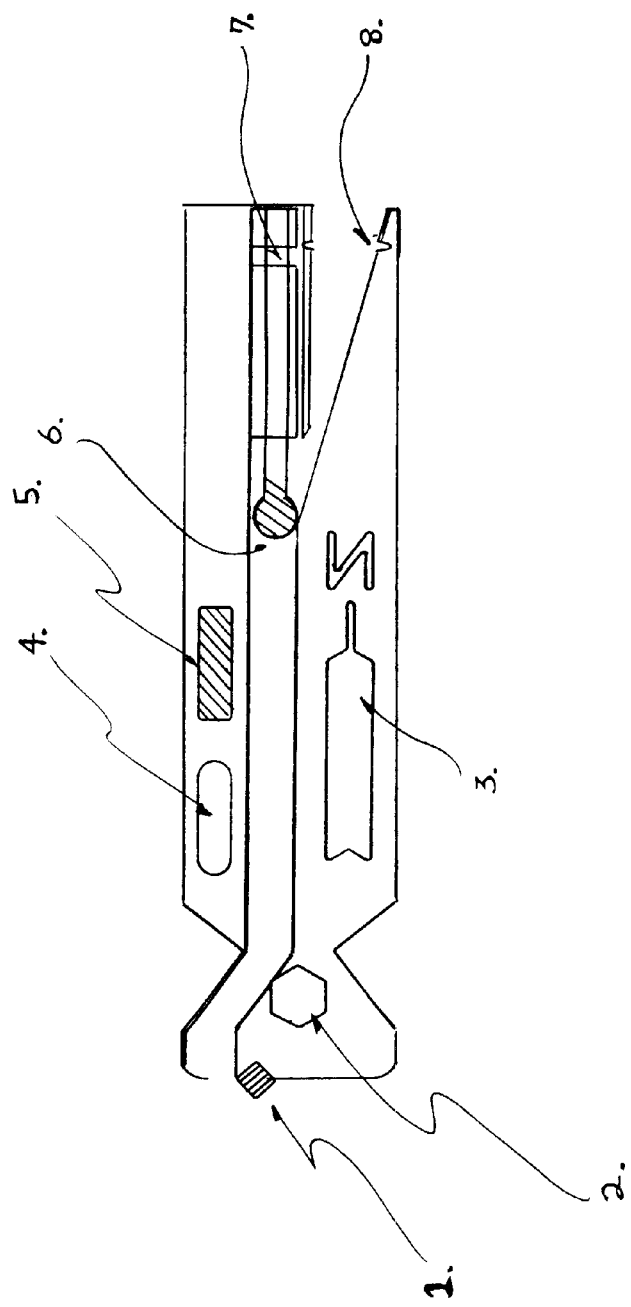
FIG. 1 shows a cross sectional representation of the implantable medical device of the present invention.

Referring now to FIG. 1, there is shown implantable medical device 10 of the present invention. Implantable medical device 10 is adapted for insertion into the bladder of an individual by way of the urinary tract. In the preferred embodiment of the invention implantable medical device 10 is matably gripped at notches 8 by a flexible tubular insertion tool for insertion within the individual. The flexible insertion tool is substantially similar to the well known shaft insertion tools used for insertion of Foley catheters. The same notches 8 can be matingly used by a removing tool in order to remove implantable medical device 10 from the urinary tract of the individual.

Using the insertion tool implantable medical device 10 is advanced through the urinary tract to the bladder. When implantable medical device 10 is inserted in this manner it is positioned with one of its ends within the bladder and one of its ends outside the bladder. In this manner the sphincter muscles of the bladder can forcibly secure implantable medical device 10 in the correct position by circumferentially gripping the outside of the housing of implantable medical device 10. In the preferred embodiment of the invention the housing of implantable medical device 10 is provided with annular recessed region 12 for gripping by the sphincter muscles of the bladder to assist in securing implantable medical device 10 in this position.

In an alternate embodiment of the invention implantable medical device 10 can be surgically positioned within the bladder of the individual rather that inserted by way of the urinary tract. Additionally, implantable medical device 10 can be stitched in its position within the individual rather than secured in its position by the sphincter muscles of the individual.

Implantable medical device 10 is adapted to assist the individual in a plurality of functions. For example, implantable medical device 10 can assist the individual in controllably permitting and preventing the flow of liquid waste from the bladder. In performing this function fluid controllably passes by way of fluid passageway 9 of implantable medical device 10.

In order to provide the various types of assistance to the individual implantable medical device 10 includes a plurality of sensing devices for determining parameters representing various conditions within the individual. For example, implantable medical device 10 includes pressure sensor 1 for determining the pressure within the bladder of the individual. Pressure sensor 1 of implantable medical device 10 can be used to determine the pressure within a bladder and to inform an individual when the bladder must be emptied. Prostate inflammation due to causes such as infection and cancer can also be monitored with pressure sensor 1 since prostate inflammation can affect bladder pressure. Furthermore, pressure sensor 1 is an operating component of implantable medical device 10 that can be used for any process or procedure using the pressure within the bladder as a parameter.

Additionally, implantable medical device 10 includes chemistry sensor 2 for performing various chemical tests and analyses of the urine within the bladder. Chemistry sensor 2 is an operating component that can determine, for example, the level of nitrates in the urine and the sugar level of the urine. Thus it is possible for the present invention to make a determination when the nitrates, sugar, or other chemicals in the urine of the individual reach an undesirable level and provide a warning to the individual.

Chemical tests monitoring the urine for indications of prostate cancer can also be performed by chemistry sensor 2. Furthermore, small chips having an extensive range of chemistry tests are available in the prior art. For example, the National Aeronautics and Space Administration and other organizations have developed a large number of such chemical chips. Any known sensors of this nature can be applied to implantable medical device 10 in order to perform any known tests upon the urine within the bladder of the individual.

The information obtained by the sensors of implantable medical device 10 can be transmitted from within the bladder of the individual to receivers outside the body using transmitter 3 when implantable medical device 10 is inserted within the bladder. Thus, information such as the bladder pressure and urine chemistry can be communicated to the individual or to medical personnel for use in caring for the individual and assisting the individual in leading a productive life. In one preferred embodiment of the invention a further pressure sensor can be provided within transmitter 3 or in the vicinity of transmitter 3. Such a pressure sensor, located outside the bladder of the individual when implantable medical device 10 is implanted, permits measurement and communication of pressure both inside and outside the bladder of the individual.

In addition to transmitter 3 implantable medical device 10 is provided with microprocessor 5. In the preferred embodiment of the invention microprocessor 5 includes a conventional radio frequency receiver. The receiver of microprocessor 5 aids in communication between implantable medical device 10 and devices outside the body of the individual when implantable medical device 10 is inserted into the bladder.

It will be understood that the various sensors, electrical components, and other operating components of implantable medical device 10 can operate under the control of microprocessor 5 in a manner well understood by those skilled in the art. Using the receiver of microprocessor 5, for example, it is possible for the individual or for medical personnel assisting the individual to apply instructions to microprocessor 5. By means of the instructions applied to microprocessor 5 it is possible to control the operations of implantable medical device 10 when it is within the body of the individual.

For example, the preferred embodiment of implantable medical device 10 includes a valve such as fluid valve 7 having valve plunger 6. Fluid valve 7 can be an electromechanical valve or any other suitable type of valve. Under the control of microprocessor 5 and the receiver therein fluid valve 7 can control the flow of fluid through fluid passageway 9 passing longitudinally through implantable medical device 10.

In order to perform this function valve plunger 6 blocks exit opening 11 and prevents fluid from flowing through exit opening 11 when it rests in its rearward position towards the end of implantable medical device 10 housing sensors 1, 2. This prevents the flow of fluid from the bladder by way of fluid passageway 9 and through the urinary tract of the individual. When valve plunger 6 is moved to its forward position exit opening 11 is no longer blocked and fluid can flow from the bladder. Thus fluid valve 7 is an operating component of implantable medical device 10 that can be useful in the treatment of urinary incontinence.

Fluid valve 7 can operate under the control of microprocessor 5. Microprocessor 5 can activate fluid valve 7 and thereby permit fluid to flow from the bladder at predetermined intervals, at scheduled times, when the pressure within the bladder reaches a predetermine level, at the instruction of the individual or medical personnel for any reason such as in response to any sensor within implantable medical device 10 such as pressure sensor 1, or in any other manner. Additionally, fluid valve 7 can be maintained in a constantly opened state if desired. In order to perform these functions signals can be applied to the receiver of microprocessor 5 from the exterior of the body as needed.

In one preferred embodiment of the invention fluid passageway 9 can be provided with a volumetric flow meter for determining the volume of fluid passing from the bladder of the individual by way of fluid passageway 9. The volume flow information can be communicated to the exterior of the body. Furthermore, microprocessor 5 can also use this information to calculate the volume of fluid flowing over a predetermined period of time, for example the flow volume over a twenty-four hour period can be determined.

Battery 4 provides power to the electrical components of implantable medical device 10 such as microprocessor 5 and transmitter 3. External energy sources can be used to recharge battery 4 in the manner known in the art. However, in the preferred embodiment of the invention battery 4 is not rechargeable. Rather implantable medical device 10 is removed from its position within the individual and battery 4 or the entire implantable medical device 10 is replaced. This is believed to be preferable because battery 4 should have a long service life and implantable medical device 10 is adapted to be easily removable and insertable. Additionally, in 11 an alternate embodiment battery 4 can be replaced in vivo without removing implantable medical device 10.

Figure 2:
FIG. 2 shows an alternate embodiment of the implantable medical device of FIG. 1.

Referring now to FIG. 2, there is shown implantable medical device 20 of the present invention. Implantable medical device 20 operates in a manner substantially similar to that described with respect to implantable medical device 10. However, the shape of implantable medical device 20 is adapted to maximize the ease of insertion and removal from the body of the individual. In order to adapt implantable medical device 20 in this manner the housing of device 20 is formed with substantially rounded corners.

The previous description of the preferred embodiments of the presennt invention is provided to enable a person skilled in the art to make and use the present invention. The various modifications to the described embodiments will be readily apparent to those skilled in the art, and the generic principles defined herein can be applied to such other embodiments without the use of the inventive faculty. For example, the implantable medical devices of the present invention can be advantageously applied to artificial bladders within individuals as well as to natural bladders as described above. Thus, the present invention is not intended to be limited to the embodiments shown herein but is to be accorded the widest scope consistent with the principles and novel features disclosed.

What is claimed is:

1. A method for communicating information between a bladder disposed within an individual and the exterior of the individual, comprising the steps of:

(a) providing an implantable medical device having a pressure sensor for sensing the pressure within the bladder, a fluid valve adapted to prevent a flow of fluid from the bladder of the individual in accordance with the sensor and a communication device for providing communication regarding the pressure between the implantable medical device and the exterior of the individual and an energy source for applying energy to the implantable medical device;

(b) inserting at least a portion of the implantable medical device into the bladder of the individual by way of the urinary tract of the individual;

(c) determining when the pressure within the bladder reaches a predetermined level and permitting fluid flow from the bladder of the individual in response to the pressure level determination;

(d) communicating the pressure level determination to the exterior of the individual by the implantable medical device;

(e) applying a control signal from the exterior of the body of the individual to the implantable medical device within the body of the individual in accordance with the communicated pressure level determination; and (f) operating the fluid valve by the implantable medical device in accordance with the control signal from the exterior of the body.

2. The method for communicating information of claim 1, wherein the implantable medical device comprises an implantable receiver for receiving date from the exterior of the body of the individual and a plurality of operating components comprising the step of receiving by the implantable receiver an instruction provided in accordance with at least one operating component and operating at least one operating component in accordance with the received instructions.

3. The method for communicating information of claim 1, wherein the implantable medical device is formed with an annular recessed region and step (b) comprises positioning the annular recessed region of the implantable medical device such that a bladder sphincter muscle surrounds and grips the annular recessed region to secure the implantable medical device.

4. The method for communicating information of claim 3, wherein the implantable medical device is secured in a position such that a portion of the implantable medical device extends into the interior of the bladder and a portion of the implantable medical device simultaneously extends into the exterior of the bladder.

5. The method for communicating information of claim 1, wherein the bladder comprises an artificial bladder.

6. The method for communicating information of claim 1, wherein the implantable medical device comprises a further pressure sensor disposed outside the bladder when the implantable medical device is inserted in the body of the individual for sensing the pressure within the bladder.

* * * * *